[19] United States Patent
Stone

[11] 4,195,085
[45] Mar. 25, 1980

[54] COMPOSITIONS AND METHODS FOR TREATING GLAUCOMA BY THE TOPICAL ADMINISTRATION OF T-BUTYLAMINO-3-(4-MORPHOLINO-1,2,5-THIADIAZOL-3-YLOXY-2-PHOPANOL HYDROGEN MALEATE

[75] Inventor: Clement A. Stone, Blue Bell, Pa.

[73] Assignee: Merck & Co., Inc., Rahway, N.J.

[21] Appl. No.: 937,696

[22] Filed: Aug. 29, 1978

Related U.S. Application Data

[63] Continuation of Ser. No. 793,817, May 4, 1977, abandoned, which is a continuation of Ser. No. 617,118, Sep. 26, 1975, abandoned.

[51] Int. Cl.² .................................................. A61K 31/535
[52] U.S. Cl. .................................................. 424/248.51
[58] Field of Search .................................. 424/248.51

[56] References Cited

U.S. PATENT DOCUMENTS

| | | | |
|---|---|---|---|
| 3,655,663 | 4/1972 | Wasson | 424/248.51 |
| 3,657,237 | 4/1972 | Weinstock et al. | 424/248.51 |
| 3,718,647 | 2/1973 | Weinstock et al. | 424/248.51 |
| 3,729,469 | 4/1973 | Wasson | 260/247.1 |
| 3,766,180 | 10/1973 | Weinstock et al. | 424/248.51 |
| 3,781,284 | 12/1973 | Weinstock et al. | 424/248.51 |
| 3,833,727 | 9/1974 | Nelson et al. | 424/248.51 |

OTHER PUBLICATIONS

Minerva Oftalmologica 14, 28–32 (1972), Bonomi, et al.
Brit. J. Ophthal. 59, 296–300 (1975), Elliot et al.
Brit. J. Ophthal. 59, 301–303 (1975), Bonomi et al.
Chem. Abst. 77, 775(w) (1972) Pecori–Giraldi et al.
Chem. Abst. 81 131,068(y) (1974)–Stankicwicy et al.
Chem. Abst. 82, 273(j)(1975)–Das et al.
Chem. Abst. 82, 26116(k) (1975), Langham et al.
Chem. Abst. 82, 38754(e) (1975), Sharaf et al.

Primary Examiner—Douglas W. Robinson
Attorney, Agent, or Firm—Edmunde D. Riedl; Mario A. Monaco

[57] ABSTRACT

Antiglaucoma compositions containing t-butylamino-3-(4-morpholino-1,2,5-thiadiazol-3-yloxy)-2-propanol hydrogen maleate and method of treating elevated intraocular pressure.

7 Claims, No Drawings

COMPOSITIONS AND METHODS FOR TREATING GLAUCOMA BY THE TOPICAL ADMINISTRATION OF T-BUTYLAMINO-3-(4-MORPHOLINO-1,2,5-THIADIAZOL-3-YLOXY-2-PHOPANOL HYDROGEN MALEATE

This is a continuation, of application Ser. No. 793,817, filed May 4, 1977, which was a continuation of application U.S. Ser. No. 617,118, filed Sept. 26, 1975, both now abandoned.

BACKGROUND OF THE INVENTION

Presently drugs such as pilocarpine and its various salts are used for the treatment of glaucoma. Although these drugs are useful they generally exhibit side effects such as extreme miosis, spasm of accomodation, night blindness and transient blurried vision. It has now been found that t-butylamino-3-(4-morpholino-1,2,5-thiadiazol-3-yloxy)-2-propanol hydrogen maleate is effective in reducing intraocular pressure both in normal and hypertensive human eyes without the side effects associated with pilocarpine type drugs.

DETAILED DESCRIPTION OF THE INVENTION

The present invention therefore relates to a method of treating glaucoma and ocular hypertension by applying an effective amount of t-butylamino-3-(4-morpholino-1,2,5-thiadiazol-3-yloxy)-2-propanol hydrogen maleate to the human or animal eye suffering from glaucoma or ocular hypertension. The invention also relates to a method of reducing normal intraocular pressure. The invention further relates to ophthalmic compositions comprising this compound.

It is a purpose of this invention to provide a novel antiglaucoma composition as well as a method of reducing intraocular pressure which partially or totally eliminates one or more of the above-mentioned side effects.

The present invention is based on the discovery that t-butylamino-3-(4-morpholino-1,2,5-thiadiazol-3-yloxy)-2-propanol hydrogen maleate decreases intraocular pressure when topically administered to the eye. The compound of this invention is a known compound useful as a β-adrenergic blocking agent as is described in U.S. Pat. Nos. 3,657,237, 3,729,469 and 3,655,663.

The compound is preferably administered in the form of ophthalmic pharmaceutical compositions adapted for topical administration to the eye such as solutions, ointments or as a solid insert. Formulations of this compound may contain from 0.01 to 5% and especially 0.5 to 2% of medicament. Higher dosages as, for example, about 10% or lower dosages can be employed provided the dose is effective in lowering intraocular pressure. As a unit dosage form between 0.001 to 5.0 mg., preferably 0.005 to 2.0 mg., and especially 0.005 to 1.0 mg. of the compound is generally applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, bacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymer.

Preferably the solid insert is prepared from cellulose derivatives such as methylcellulose, hydroxyethyl cellulose, hydroxypropyl cellulose or hydroxypropylmethyl cellulose or from other synthetic materials such as polyvinyl alcohol, polyvinyl pyrrolidone, polyethylene oxide or polyvinyl methylether. Hydroxypropyl cellulose, one of the preferred polymers for the preparation of the insert is available in several polymeric forms, all of which are suitable in the preparation of these inserts. Thus, the product sold by Hercules, Inc. of Wilmington, Delaware under the name KLUCEL such as KLUCEL HF, HWF, MF, GF, JF, LF and EF which are intended for food or pharmaceutical use are particularly useful. The molecular weight of these polymers useful for the purposes described herein may be at least 30,000 to about 1,000,000 or more. Similarly, an ethylene oxide polymer having a molecular weight of up to 5,000,000 or greater, and preferably 100,000 to 5,000,000 can be employed. Further, for example, POLYOX a polymer supplied by Union Carbide Co. may be used having a molecular weight of about 50,000 to 5,000,000 or more and preferably 3,000,000 to 4,000,000. Other specific polymers which are useful are polyvinyl pyrrolidine having a molecular weight of from about 10,000 to about 1,000,000 or more, preferably up to about 350,000 and especially about 20,000 to 60,000; polyvinyl alcohol having a molecular weight of from about 30,000 to 1,000,000 or more, particularly about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 100,000; and CARBOPOL (carboxyvinyl polymer) of B. F. Goodrich and Co. designated as grades 934, 940 and 941. It is clear that for the purpose of this invention the type and molecular weight of the polymer is not critical. Any water soluble polymers can be used having an average molecular weight which will afford dissolution of the polymer and accordingly the medicament in any desired length of time. The inserts, therefore, can be prepared to allow for retention and accordingly effectiveness in the eye for any desired period. The insert can be in the form of a square, rectangle, oval, circle, doughnut, semi-circle, ¼ moon shape, and the like. Preferably the insert is in the form of a rod, doughnut, oval or ¼ moon. The insert can be readily prepared, for example, by dissolving the medicament and the polymer in a suitable solvent and the solution evaporated to afford a thin film of the polymer which can then be subdivided to prepare inserts of appropriate size. Alternatively the insert can be prepared by warming the polymer and the medicament and the resulting mixture molded to form a thin film. Preferably, the inserts are prepared by molding or extrusion procedures well known in the art. The molded or extruded product can then be subdivided to afford inserts of suitable size for administration in the eye. The insert can be of any suitable size to readily fit into the eye. For example, castings or compression molded films having a thickness of about 0.25 mm. to 15.0 mm. can be subdivided to obtain suitable inserts. Rectangular segments of the cast or compressed film having a thickness between about 0.5 and 1.5 mm. can be cut to afford shapes such as rectangular plates of 4×5-20 mm. or ovals of comparable size. Similarly, extruded rods having a diameter between about 0.5 and 1.5 mm. can be cut into suitable sections to provide the desired amount of polymer. For example, rods of 1.0 to 1.5 mm. in diameter and about 20 mm. long are found to be satisfactory. The inserts may also be directly formed by injection molding. It is preferred that the ophthalmic inserts containing the medicament of the present invention be formed so that they are smooth and do not have any sharp edges or corners which could cause damage to the eye. Since the term smooth and sharp edges or corners are subjective terms, in this application these terms are used to indicate that excessive irritation of the eye will not result from the use of the insert.

The ocular medicinal inserts can also contain plasticizers, buffering agents and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from up to 1 about 30% by weight. A particularly preferred plasticizer is water which is present in amounts of at least about 5% up to about 40%. In actual practice, a water content of from about 10% to about 20% is preferred since it may be easily accomplished and adds the desired softness and pliability to the insert.

When plasticizing the solid medicinal product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohol and phenylethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates, and the like, such as sodium phosphate, citrate, borate, acetate, bicarbonate and carbonate. These agents may be present in amounts sufficient to obtain a pH of the system of between 5.5 to 8.0 and especially 7-8; usually up to about 2% by weight of polymer. The insert may contain from about 1 mg. to 100 mg. of water soluble polymer, more particularly from 5 to 50 mg. and especially from 5 to 20 mg. The medicament is present from about 0.1 to about 25% by weight of insert.

The hydrogen maleate compound has been studied with respect to its ability to lower intraocular pressure of rabbits with experimental glaucoma induced by intraocular injection of $\alpha$-chymotrypsin. This study demonstrated that the compound is very effective in lowering intraocular pressure after topical application. Pressure was reduced in the normal and the glaucomatous eye.

The following examples are given by way of illustration.

EXAMPLE 1

| Solution Composition | | |
|---|---|---|
| t-Butylamino-3-(4-morpholino-1,2,5-thiadiazol-3-yloxy)-2-propanol hydrogen maleate (I) | 1 mg. | 15 mg. |
| Sodium phosphate monobasic .2H$_2$O | 9.38 mg. | 6.10 mg. |
| Dibasic sodium phosphate .12H$_2$O | 28.48 mg. | 16.80 mg. |
| Benzalkonium chloride | 0.10 mg. | 0.10 mg. |
| Sodium hydroxide q.s. | pH 6.8 | pH 6.8 |
| Water for injection q.s. ad. | 1.0 ml. | 1.0 ml. |

(I), phosphate buffer salts, and benzalkonium chloride are added to and dissolved in water. The pH of the solution is adjusted to 6.8 with sodium hydroxide and the final solution diluted to volume. The solution is rendered sterile by filtration through a sterilizing filter.

EXAMPLE 2

| | |
|---|---|
| t-Butylamino-3-(4-morpholino-1,2,5-thiadiazol-3-yloxy)-2-propanol hydrogen maleate (I) | 5 mg. |
| Petrolatum q.s. ad. | 1 gram |

Compound (I) and the petrolatum are aseptically combined.

EXAMPLE 3

| | |
|---|---|
| t-Butylamino-3-(4-morpholino-1,2,5-thiadiazol-3-yloxy)-2-propanol hydrogen maleate (I) | 1 mg. |
| Hydroxypropylcellulose q.s. | 12 mg. |

Ophthalmic inserts are manufactured from compression molded films which are prepared on a Carver Press by subjecting the powder mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for ½ hour.

EXAMPLE 4

| | |
|---|---|
| t-Butylamino-3-(4-morpholino-1,2,5-thiadiazol-3-yloxy)-2-propanol hydrogen maleate (I) | 1 mg. |
| Hydroxypropyl cellulose q.s. ad. | 12 mg. |

Ophthalmic inserts are manufactured from a solvent cast film prepared by making a viscous solution of the powder using methanol as the solvent. The solution is placed on a Teflon plate and allowed to dry at ambient conditions. After drying, the film is placed in an 88% R.H. cabinet until it is pliable. Appropriately sized inserts are cut from the film.

EXAMPLE 5

| EXAMPLE 5 | |
|---|---|
| t-Butylamino-3-(4-morpholino-1,2,5-thiadiazol-3-yloxy)-2-propanol hydrogen maleate (I) | 1 mg. |
| Hydroxypropyl methyl cellulose q.s. ad. | 12 mg. |

Ophthalmic inserts are manufactured from a solvent cast film which is prepared by making a viscous solution of the powder blend using a methanol/water solvent system (10 ml. methanol is added to 2.5 g. of powder blend, to which 11 ml. of water (in three divided portions) is added. The solution is placed on a Teflon plate and allowed to dry at ambient conditions. After drying, the film is placed in an 88% R.H. cabinet until it is pliable. Appropriately sized inserts are then cut from the film.

EXAMPLE 6

| | |
|---|---|
| t-Butylamino-3-(4-morpholino-1,2,5-thiadiazol-3-yloxy)-2-propanol hydrogen maleate (I) | 1 mg. |
| Hydroxypropylmethyl cellulose q.s. ad. | 12 mg. |

Ophthalmic inserts are manufactured from compression molded films which are prepared on a Carver Press by subjecting the powder mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for one-half hour.

What is claimed is:

1. A method for treating glaucoma and for lowering intraocular pressure which comprises topically applying to the glaucomatous eye an intraocular pressure lowering effective amount of t-butylamino-3-(4-morpholino-1,2,5-thiadiazol-3-yloxy)-2-propanol hydrogen maleate.

2. A method according to claim 1 wherein the t-butylamino-3-(4-morpholino-1,2,5-thiadiazol-3-yloxy)-2-propanol is administered in a water soluble polymeric insert.

3. A method according to claim 2 wherein the polymer is hydroxypropylcellulose.

4. A method according to claim 1 wherein the t-butylamino-3-(4-morpholino-1,2,5-thiadiazol-3-yloxy)-2-propanol is administered as a 0.01 to 5% solution of t-butylamino-3-(4-morpholino-1,2,5-thiadiazol-3-yloxy)-2-propanol in an ophthalmologically acceptable carrier.

5. An ophthalmic composition for the topical treatment of glaucoma comprising in solution an intraocular pressure lowering effective amount of t-butylamino-3-(4-morpholino-1,2,5-thiadiazole-3-yloxy)-2-propanol hydrogen maleate and a liquid ophthlamic carrier.

6. A composition according to claim 5 wherein the solution is from 0.01 to 5% t-butylamino-3-(4-morpholino-1,2,5-thiadiazol-3-yloxy)-2-propanol hydrogen maleate.

7. A composition according to claim 5 wherein the solution is from 0.5 to 2% t-butylamino-3-(4-morpholino-1,2,5-thiadiazol-3-yloxy)-2-propanol hydrogen maleate.

* * * * *